United States Patent [19]

Smith

[11] Patent Number: 5,666,950
[45] Date of Patent: Sep. 16, 1997

[54] FILTER DEVICE FOR A TRACHEOSTOMA

[75] Inventor: Rory James Maxwell Smith, Skipton, Great Britain

[73] Assignee: Kapitex Healthcare Ltd., Wetherby, United Kingdom

[21] Appl. No.: 362,603

[22] PCT Filed: Jul. 8, 1993

[86] PCT No.: PCT/GB93/01428

§ 371 Date: Mar. 21, 1995

§ 102(e) Date: Mar. 21, 1995

[87] PCT Pub. No.: WO94/01199

PCT Pub. Date: Jan. 20, 1994

[30] Foreign Application Priority Data

Jul. 10, 1992 [GB] United Kingdom .................. 9214716

[51] Int. Cl.[6] .................... A62B 19/00; A61M 16/04
[52] U.S. Cl. ................ 128/207.14; 128/207.29; 128/205.29; 128/204.17; 128/201.13; 623/9
[58] Field of Search ................ 623/9; 128/207.29, 128/205.28, 205.29, 203.26, 204.17, 207.14, 201.25, DIG. 26, 207.16, 201.13

[56] References Cited

U.S. PATENT DOCUMENTS

| | | | |
|---|---|---|---|
| 3,920,009 | 11/1975 | Olsen | 128/205.29 |
| 4,382,440 | 5/1983 | Kapp et al. | 128/205.29 |
| 4,463,757 | 8/1984 | Schmidt | 128/205.29 |
| 4,687,482 | 8/1987 | Hanson | 623/9 |
| 4,883,052 | 11/1989 | Weiss et al. | 128/205.27 |
| 4,971,054 | 11/1990 | Andersson et al. | 128/207.14 |
| 5,022,394 | 6/1991 | Chonielinski | 128/207.14 |
| 5,186,165 | 2/1993 | Swann | 128/201.25 |

FOREIGN PATENT DOCUMENTS

| | | |
|---|---|---|
| 0294707 | 12/1988 | European Pat. Off. |
| 2583290 | 12/1986 | France |
| 3733389 | 4/1989 | Germany |
| 2028664 | 3/1980 | United Kingdom |
| 2214089 | 8/1989 | United Kingdom |
| 9105579 | 5/1991 | WIPO |

*Primary Examiner*—Vincent Millin
*Assistant Examiner*—V. Srivastava
*Attorney, Agent, or Firm*—Merchant, Gould, Smith, Edell, Welter & Schmidt, P.A.

[57] ABSTRACT

A device for filtering air that is to be breathed through a tracheostoma, to simulate the role of the nose particularly in patients who have received a tracheostomy comprises a filter (20). The filter comprises a pre-filter (21) formed from electrostatically charged fibers, a first layer (22) formed from activated carbon and a second layer (23) a hydrophilic material such as one that is based on regenerated cellulose material. The filter includes a layer of adhesive by which it can be held in place when in use, and a cover layer (24) on its exposed surface.

18 Claims, 5 Drawing Sheets

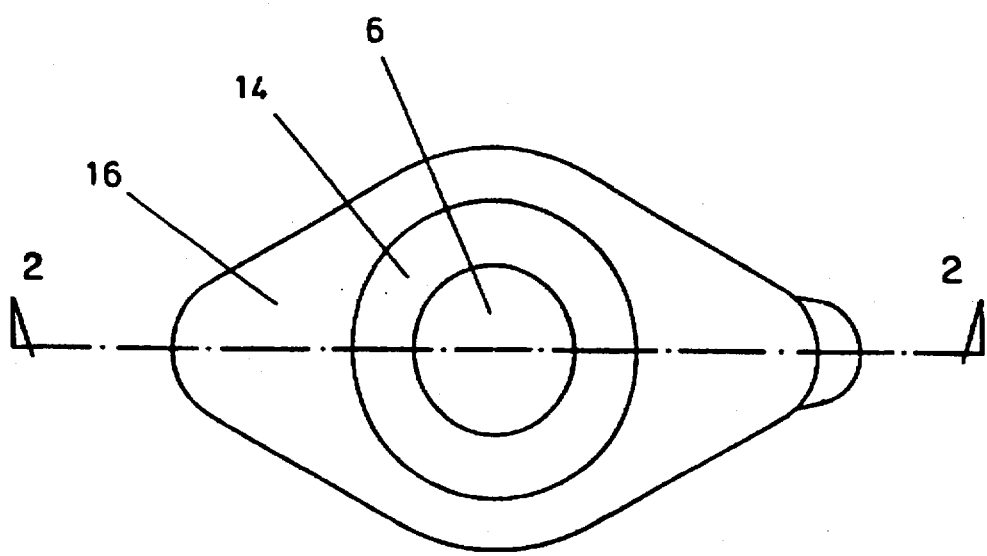
FIG. 1
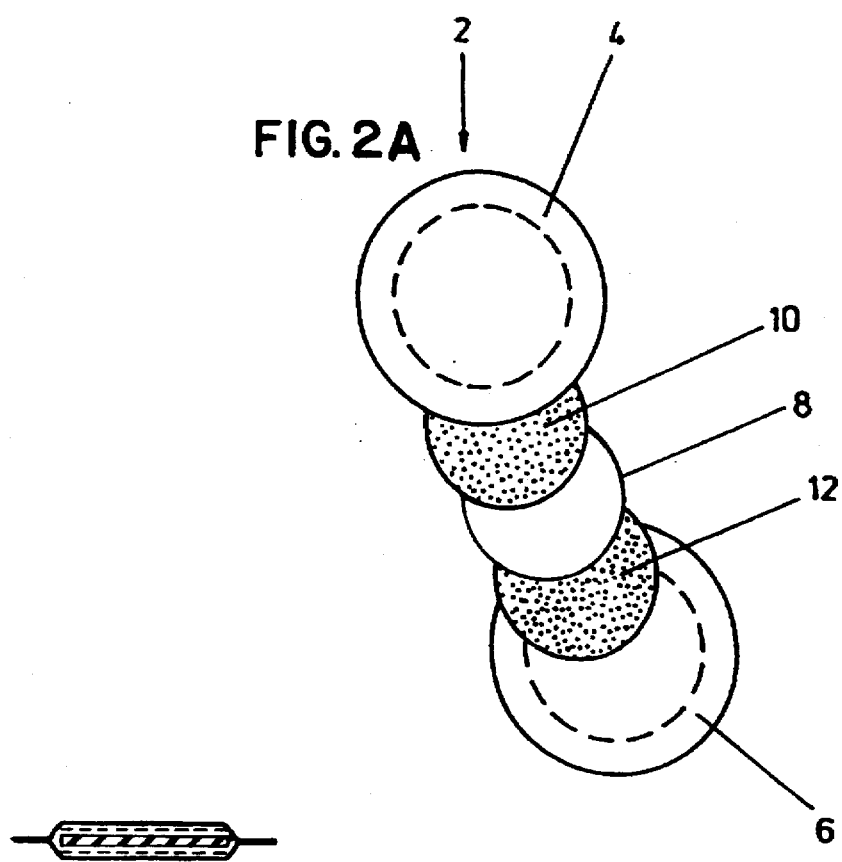
FIG. 2A
FIG. 2

FILTER DEVICE FOR A TRACHEOSTOMA

BACKGROUND OF THE INVENTION

1. Field of the Invention

This invention relates to a filter device for filtering air that is to be breathed through a tracheostoma, for example in patients who have received a tracheostomy, for example as part of a laryngectomy. Under such circumstances, the device can be fitted over a tracheostoma, body worn, for example directly over a tracheostoma, or to a tracheostomy tube, and serves to simulate some of the functions of the nose. The device can include a valve to assist in diverting the flow of exhaled air, for example to permit speech.

2. Description of Related Art

A tracheostomy is a surgical procedure in which an opening is formed through the anterior surface of the neck into the trachea. The opening is referred to as a tracheostoma. A tracheostomy tube can be provided to extend between the tracheostoma and the trachea.

A laryngectomy is a surgical procedure, used for example to treat a carcinoma, which involves removal of the larynx or voice box and creation of a tracheostoma. A consequence of the procedure is that the trachea is no longer connected to the pharynx but is diverted to the tracheostoma. After this procedure, normal nasal function is not possible.

In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and micro organisms, from the inhaled airstream, and the action of cilia transports mucous and any particles away from the lungs.

The exchange of heat and moisture, and filtration are clearly beneficial to the patient and, in their absence, clinical consequences such as increased incidence of chest infections, elevated levels of secretion production and encrustation are observed.

The upper airways also provide resistance to air flow which promotes good thoracic muscle tone and allows good respiratory function to be maintained.

A further consequence of a laryngectomy is that speech is no longer available by the normal method of passage of air through the vocal cords of the larynx. Where clinical conditions permit, it is clearly in the patient's interest to restore the facility of speech.

It is sometimes possible to insert a voice prosthesis in an artificially created fistula between the upper regions of the trachea and the oesophagus. It then becomes necessary to provide means for directing the flow of exhaled air through the voice prosthesis. This can be conveniently achieved by the incorporation of a valve in an externally worn device.

When a patient has received a tracheostomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the patient to speak. It is desirable that the flow of the exhaled air be controlled by means of a tracheostoma valve. In these situations, the valve can be arranged to remain open during breathing but, with a small additional increase in exhaled air pressure, can be closed to divert the air flow.

SUMMARY OF THE INVENTION

In one aspect, the invention provides a filter device for filtering air that is to be breathed through a tracheostoma, which comprises:

(a) a first zone for filtering matter filtered in a normal nasal cavity from air passing through the filter; and (b) a second zone having means for exchange of heat and moisture with the air.

The first and second zones of the filter may comprise separate first and second layers which are juxtaposed one on top of the other and preferably attached to one another. In another construction, the zones may by provided by zones within a single layer. The single layer device may be formed by a process which involves carding.

The second zone of the filter is moisturised and warmed by exhaled air. The moisture and warmth collected by the second zone is then imparted to inhaled air, which is filtered by the first zone. Generally, the air is filtered by the first zone before it is moisturised and warmed by the second zone, especially when the filter comprises two layers.

Preferably, the resistance to air flow through the device of the invention is at least about $0.2$ $kPa.s.l^{-1}$, more preferably at least about $0.4$ $kPa.s.l^{-1}$. Preferably, the resistance is not more than about $2.0$ $kPa.s.l^{-1}$, more preferably less than about $1.5$ $kPa.s.l^{-1}$, especially less than about $1.0$ $kPa.s.l^{-1}$, for example about $0.7$ $kPa.s.l^{-1}$. The resistance to air flow can be adjusted by selection of materials for the component parts of the filter device, consistent with the parts satisfying other requirements such as filtration and heat and moisture exchange.

Resistance to air flow in breathing can be measured using rhinomanometry, for example as disclosed in Journal of Laryngology and Orology, August 1987, vol 101, pp 800 to 808. When resistance to air flow breathed through a tracheostoma is to be measured, the method is modified by inserting the tube of the rhinomanometer into the tracheostoma under the edge of a filter device, where it is sealed using a grommet. A mask is placed over the tracheostoma and the filter device. The pressure gradient across the filter device is determined by measuring the pressures inside and outside the filter device, respectively. The resistance to air flow can then be calculated as described in the paper.

The first zone filters matter from air passing through the filter which is filtered in a normal nasal cavity. Such matter will generally include fine particles, micro organisms, and pollutants.

Preferably, the first zone of the filter comprises an activated carbon material. Such a material can be produced by heating material such as a rayon viscose fabric to carbonise it and to make it porous and absorbent. Such material can have a filter size of less than about $10^{-7}$ m, and an internal surface of area of greater than $1000$ $m^2.g^{-1}$, for example about $1200$ $m^2.g^{-1}$.

An advantage of the use of a carbon material in the filter zone of the device is that good filtration of small particles (including for example bacteria) and absorption of gases can be achieved while not increasing the resistance to air flow through the device. Indeed, it has been found that the resistance to air flow through a device which uses a carbon material in the filter zone can resemble very closely that of the human nose, while maintaining good filter and adsorption performance. A further advantage is that, because of the mechanism of adsorption of certain materials onto a carbon material, some heat exchange can take place.

The carbon can be provided on the surface of or in the interstices of a carrier, which might be for example a foam or fibrous material.

The carbon can be provided as a fabric, for example a woven, non-woven or knitted fabric. A fabric formed from an activated carbon has a strand-like formation which gives a high external surface area, which enhances the level of diffusion of gases through the cloth.

The carbon of the first zone can be modified to augment its filtration characteristics, for example by impregnation with silver in order to enhance its properties in relation to bacteria.

The first zone of the filter can be provided by a fabric formed from fine fibres, such as one formed from microfibres which have a diameter of less than about 25 µm, more preferably less than about 20 µm, especially less than about 12 µm, for example about 4 to 10 µm. Such fibres can be formed into a non-woven fabric sheet. A suitable fabric for use in the first zone of the filter is electrostatically charged, especially positively charged.

A component of the filter that is formed from microfibres can include one or more support layers. For example, a layer formed from microfibres can be located between two layers of coarsely woven fibres.

The second zone will generally comprise a hydrophilic material, and indeed in many circumstances can consist virtually entirely of one or more such materials, other than materials intended for example to assist in stabilising the construction of the zone. The second zone can comprise fibrous material, such as material incorporated into a woven, non-woven or knitted fabric. Suitable materials can include those based on regenerated cellulose material, especially viscose rayon or polyester, or a fabric formed from a blend of such fibres, and materials based on acrylic acid and its derivatives, for example in powder, gel or fibrous form.

Preferably, the filter size of the first zone is greater than about $0.5 \times 10^{-6}$ m, preferably greater than about $10^{-6}$ m. Filter size is measured by directing an air stream at a sheet of material. The stream contains particles with a particle size profile that has been established using a particle counter such as that sold under the trade mark ROYCO. The particle size profile resulting from passage of the air stream through the sheet is measured and compared with that of the incident stream, and the effective pore size is the size of the smallest particles of which 80% are retained by the sheet. It will be understood that this test is applicable to materials which have pores (such as microporous membranes) and to materials which do not have pores in the strict sense.

The device of the invention may include a pre-filter having a filter size that is larger than that of the first zone of the filter. The pre-filter will generally comprise fibrous material.

When the second zone of the filter is located outside the first zone (so that air is moisturised and warmed in the second zone before it is filtered in the first zone), the second zone can provide the pre-filter. More than one zone which includes means for exchange of heat and moisture with the air can be provided, of which at least one can be located outside the first zone of the filter to function as a pre-filter. When more than one such zone is provided, the materials of the zones can be the same or different.

The pre-filter can be formed from fine fibres, especially the microfibres as referred to above.

A fibrous pre-filter preferably has a weight of greater than about 10 g.m$^{-2}$, more preferably greater than about 15 g.m$^{-2}$. The weight is preferably less than about 95 g.m$^{-2}$, more preferably less than about 65 g.m$^{-2}$, for example about 45 g.m$^{-2}$.

Preferably, the fibres of the pre-filter are electrostatically charged, which has been found to assist filtration.

In another aspect, the invention provides a filter device for filtering air that is to be breathed through a tracheostoma, which comprises:

(a) a pre-filter zone, and (b) a zone for filtering matter filtered in a normal nasal cavity from air passing through the filter, the filter size of the filter zone being smaller than that of the pre-filter zone.

Preferably, the filter size of the pre-filter is more than about $5 \times 10^{-6}$ m, more preferably more than about $10 \times 10^{-6}$ m, especially more than about $15 \times 10^{-7}$ m.

Preferably, the ratio of the filter size of the pre-filter to that of the first zone of the filter is greater than about 5, more preferably less than about 10, especially less than about 15.

Suitable materials for the pre-filter include polyolefins, especially polypropylenes, and polycarbonates.

Preferably, the device includes at least one cover layer, which can to protect the filter during assembly and when in use. The cover layer might provide, for example, the protection for a pre-filter formed from fine fibres.

More than one cover layer can be provided; for example separate cover layers can be provided, one on each face of the device. The materials of cover layers provided on respective faces of the device can be different from one another.

When the device includes more than one layer of material, for example when the first and second zones are separate layers, or when the device includes one or both of a pre-filter or a cover layer, adjacent ones of the layers may be held in place relative to one another, for example by means of adhesive, by welding or by mechanical fastening means. Suitable adhesives include materials which can be activated by the application of heat, such as fusible materials. Such materials can be incorporated into or placed on one of the layers, or may be placed between adjacent layers.

The filter of the invention can be formed as a single layer, whose properties change from one zone to another. This might be achieved, for example, by means of a carding machine. For example, a composite non-woven fabric can be formed by first laying down fibres of two materials in two layers, and then causing the layers to bond to one another by means of needles or by fine jets of water at high pressure.

A dual rotor carding method can be used to form a single layer product with more than one zone, in which two distinct fibre types are presented to a single dual rotor card, which can be used to form a product in which the fibre type changes gradually through the thickness of the product, for example from 100% filter—0% hydrophilic fibre on one surface to 0% filter—100% hydrophilic fibres on the opposite surface. The composite structure can subsequently be consolidated, for example by treatment with a consolidating substance (which might be an adhesive) or by physical means such as heating.

Preferably, the device includes means for sealing the device around the stoma, allowing the device to be body worn. The seal might be directly to the skin around the stoma or to a substrate component which is mounted already. The seal will frequently extend around the stoma completely and continuously, although there will be many situations in which it will be satisfactory for the seal to extend only partially around the stoma, provided that the device is not able to move significantly during normal physical activities away from the stoma to the extent that foreign particles can enter the stoma.

A seal can suitably be provided by a quantity of an adhesive material which can be exposed to mount the filter for use. A device that is mounted by means of adhesive can be relatively inconspicuous, and can for instance be disguised under normal clothing.

The adhesive may be provided to surround the stoma completely, or it may be provided to form a seal around part only of the stoma, for example as a adhesive strip which extends along one side, or two opposite sides, or three sides, of the stoma.

Preferably, the adhesive comprises a composition which absorbs significant quantities of moisture and can therefore reduce skin maceration, for example a hydrocolloid composition. It can be convenient in some circumstances to include in the device a quantity of a hydrocolloid composition together with another adhesive material with different properties, for example a higher initial tackiness.

The device may include a web of material to which the filter is attached, which is coated with an adhesive for mounting the filter for use. A suitable web might be an adhesive coated tape.

Preferably, the adhesive material is provided on a surface of a component of the device in selected regions of the surface, which can facilitate moisture vapour transmission, for example when the adhesive that is used does not absorb significant quantities of moisture.

Alternatively or in addition to the use of an adhesive, the device may be held in place by components such as a tape, a tie, or strips of an interengaging hook and loop material (such as that sold under the trade mark VELCRO).

The filter device can be arranged to operate with a valve, which might be relied on, for example, to divert exhaled air for generation of speech. The valve will generally be mounted outside the filter component of the device. The incorporation of a valve in the device can obviate the need for manual occlusion in order to divert air flow.

A valve can be attached to the external surface of the device. For example, the device might include formations for engaging a valve. These might take the form of, for example, a socket, a bayonet or other twist lock fitting, or a threaded fastener portion. This is particularly advantageous when the filter device is secured in place next to a stoma by means of an adhesive around the filter to provide a seal.

Preferably, the filter device includes a housing for a valve. Such a housing can be can be attached to the outer surface of the device during assembly, for instance, by welding. The housing can receive a tracheostoma valve in it, for example by means of cooperating flanges, and can enable the valve to be attached and detached conveniently and while also providing an air tight seal to the filter, and thereby to the stoma itself.

It is also envisaged that a valve might be attached to the filter by means of adhesive.

A valve might be provided in a housing which is formed integrally with, or is connected to, means for mounting the device onto a tracheostoma. The housing can include means for receiving a filter component which includes a first zone for filtering matter filtered in a normal nasal cavity from air passing through the filter; and (a) a second zone having means for exchange of heat and moisture with the air, or (b) a pre-filter zone, or both. For example, the housing might include a slot in which a filter component can be received. A filter component might be fitted between the housing and the mounting means with which the housing engages.

The device can be fitted to the exposed end of a tracheostomy tube by an appropriate attachment device. Such a attachment device might comprise:

(a) a first component that can engage the filter device and can be fitted around the external circumference of the tube; and (b) a second component which can engage the first component and the external circumference of the tube to provide an air-tight seal.

A suitable attachment device is disclosed in the application filed with the present application bearing the reference P21558WO which claims priority from UK patent application no. 9214716.4, and which is entitled Tracheostomy tube assembly. Subject matter disclosed in the specification of that application is incorporated in this specification by this reference.

BRIEF DESCRIPTION OF THE DRAWINGS

Embodiments of the invention will now be further described by way of example only, with reference to the accompanying drawings in which:

FIG. 1 is a schematic representation of a filter;

FIG. 2 is an exploded view of the layers of the filter of FIG. 1;

DETAILED DESCRIPTION OF THE ILLUSTRATED EMBODIMENTS

Figure 3:
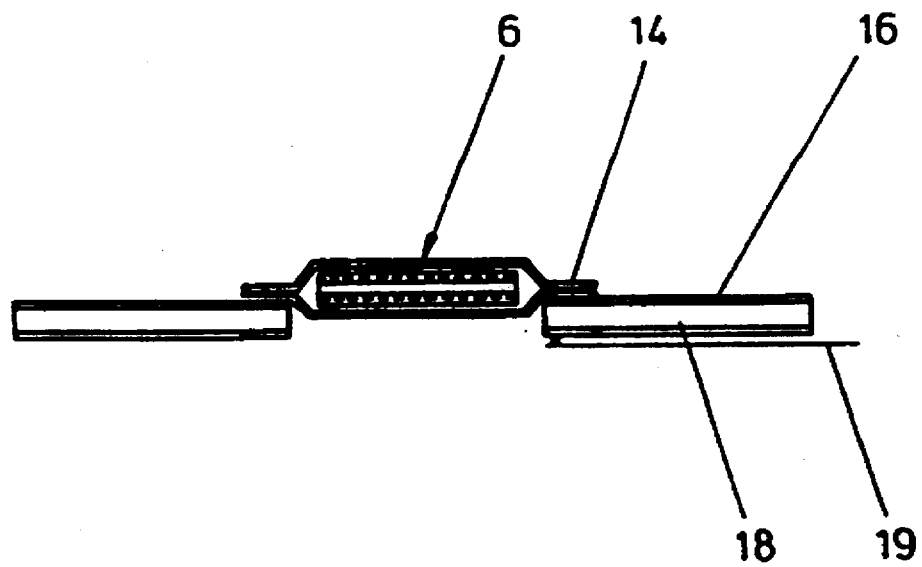
FIG. 3 is a cross-section along A—A of FIG. 1.

Referring to the drawings, FIGS. 1 to 3 show a filter 2 which comprises five layers. The outer cover layer 4 is provided by a non-woven nylon fabric, with an acrylic binder. The inner cover layer 6 is provided by a perforated polyethylene film. The central layer 8 is provided by a non-woven polyester fabric which has been impregnated with carbon. Intermediate layers 10, 12 are provided between the cover layers 4, 6 and the central layer 8, provided by a non-woven fabric formed from a blend of viscose rayon and polyester.

The central layer 8 of the filter provides a first zone in which particulate matter, pollutants and micro organisms can be filtered from air passing through the filter. The intermediate layer 10 provides a pre-filter whose filter size is larger than that of the first zone of the filter. The hydrophilic fibres of the intermediate layer 12 provide means for exchange of heat and moisture with the air.

The filter provided by the central and intermediate layers are located between the two cover layers, whose area is bigger than that of the central and intermediate layers. The cover layers are attached by means of a radio frequency weld around their periphery 14 to a backing sheet 16 (such as a non-woven backing sheet formed from polyethylene), which is coated with a hydrocolloid adhesive material 18. A release paper 19 is provided to protect the adhesive material before the filter is positioned for use on the skin of a user over the stoma.

Figure 4:
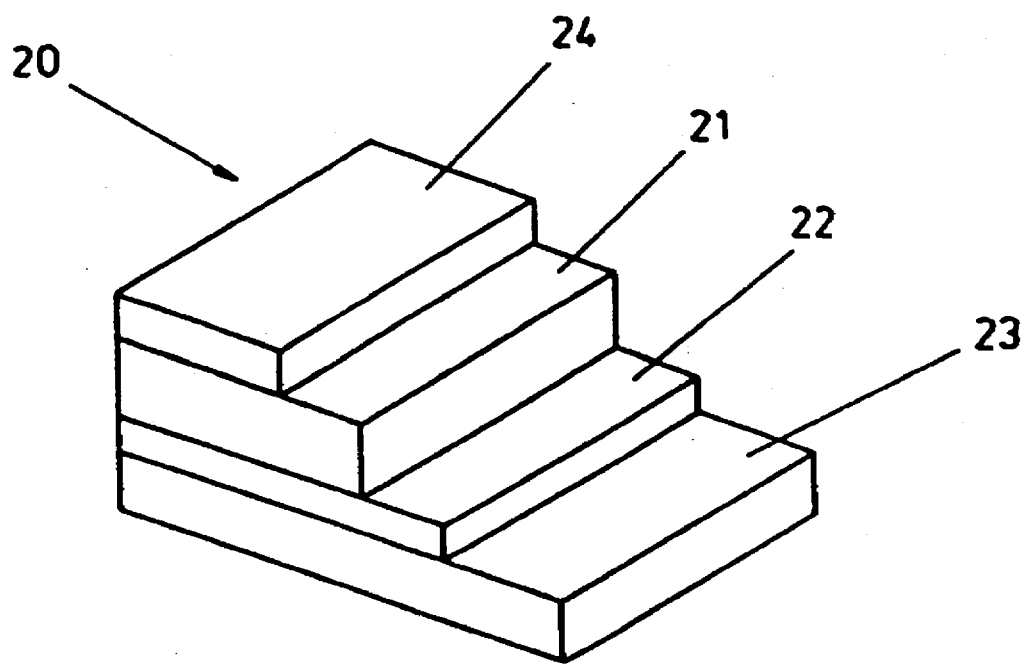
FIG. 4 is an exploded isometric view of another embodiment of filter.

FIG. 4 shows a filter device 20 which comprises a pre-filter 21 formed from electrostatically charged microfibres, a first zone 22 formed from activated carbon and a second zone 23 formed from viscose fibres. The filter further comprises a cover layer 24.

In use, the second zone 23 is positioned adjacent a stoma in a patient who has had a tracheostomy. The cover stock layer 24 is exposed to the environment.

The first zone 22 comprises a layer of activated carbon cloth. Such a layer has a high surface area and is able to filter bacteria, and to absorb certain pollutant gases such as hydrogen sulphide. The second zone 23 is comprises fibres of a hydrophilic material such as viscose.

Figure 5:
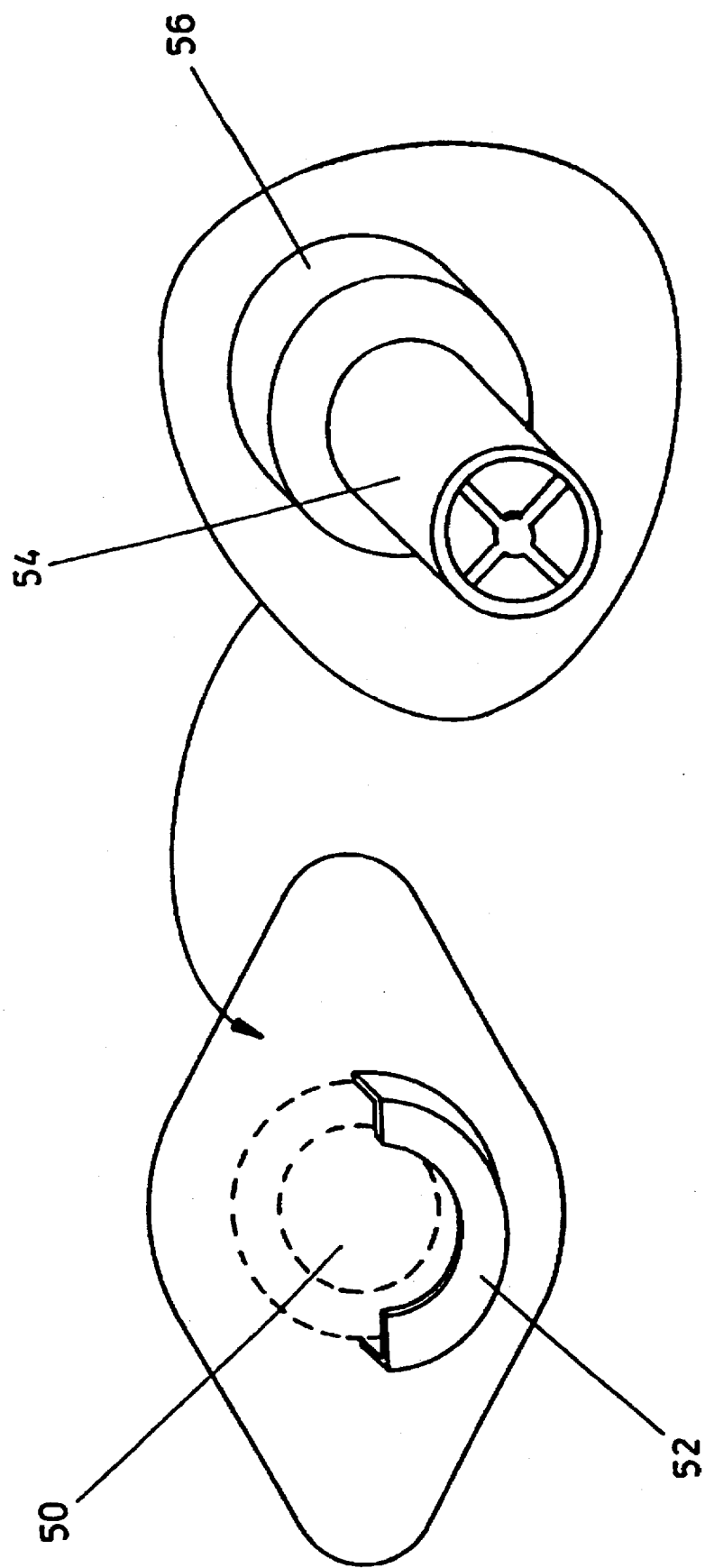
FIGS. 5 and 6 are views of filter devices which include means for engaging a valve.

FIG. 5 shows a filter device 50 which includes a socket 52 for receiving a tracheostomy valve 54. The socket is open at its upper end, and can receive a flange 56 on the valve. The socket is fastened to the filter device by welding.

Figure 6:
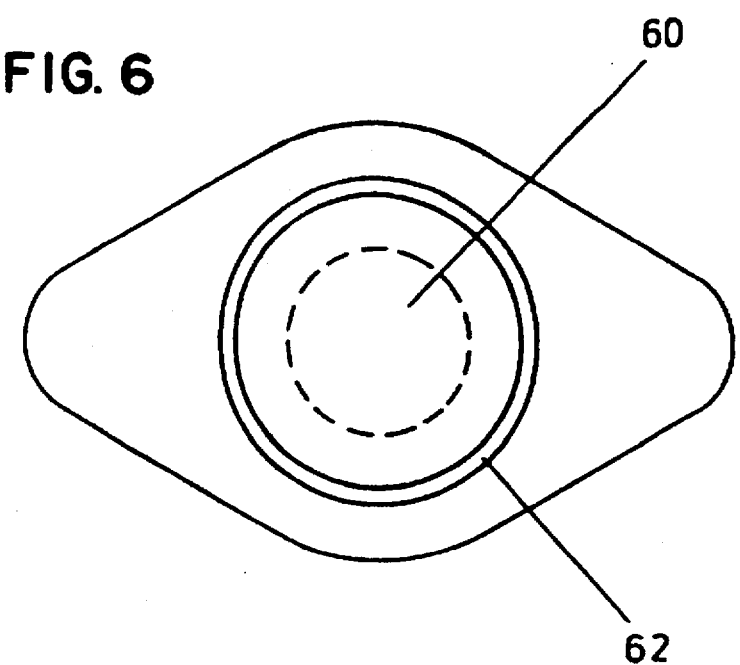

FIG. 6 shows a filter device 60 which includes an upstanding flange 62 for engaging a tracheostomy valve. The flange can be threaded to engage the valve, or it might be continuous and engage a matable flange on the valve by deformation of one or both of the flanges, for example in the manner of a container used for storage of food.

Figure 7:
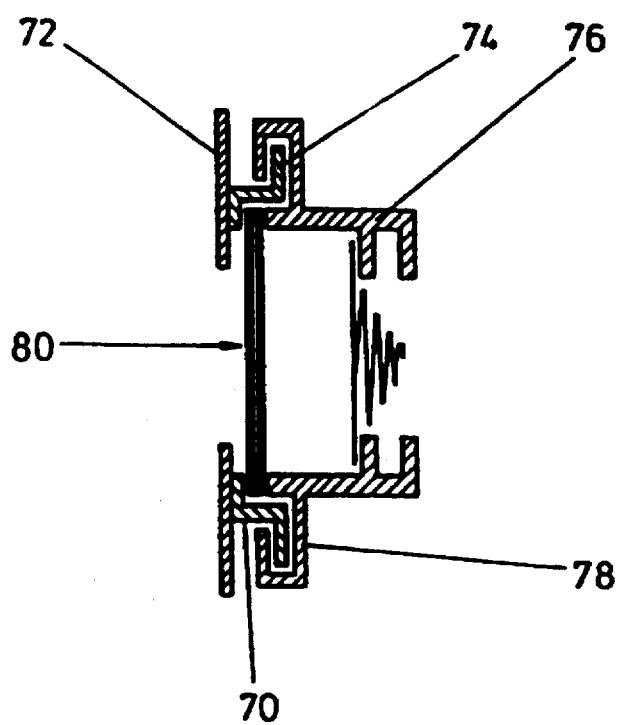
FIG. 7 is a side cross sectional view of a filter device in which the filter component is held in place between a valve housing and a mounting flange.

FIG. 7 shows a filter device which comprises a mounting component 70 having a layer of an adhesive material on the surface 72 which is intended to contact the skin of a patient around a tracheostoma. The mounting component has a flange 74 extending from it. The device includes a housing 76 for a valve, the housing including a cooperating flange 78 to engage the flange 74 on the mounting component. In alternative arrangement, the mounting component and the housing can be attached to one another by means of an adhesive.

A filter component 80, which might comprise the five layers shown in FIG. 2, or the four layers shown in FIG. 4, is held in place between the mounting component 70 and the housing 76 when the two are mated with one another.

The housing might include a slot or other formation for receiving the filter component, so that the filter component can be removed from the filter device and replaced, without removal of the housing from the stoma. Indeed, especially in this arrangement, the housing and the mounting component might be provided by a single component.

EXAMPLE

A filter having the construction shown in and described with reference to FIGS. 1 to 3 was made using the following materials:

| Central layer 8 | |
| --- | --- |
| Fabric construction | Non-woven polyester fabric impregnated with carbon |
| Carbon content | 90 to 110 g · m$^{-2}$ |
| Thickness | 0.5 to 1.0 mm |
| Air permeability | 100 to 160 cc · cm$^{-2}$ · s$^{-1}$ (Method BS 5636) |
| Surface pore size | 200 × 10$^{-9}$ m |
| Surface area | 1000 to 1300 m$^{-2}$ · g$^{-1}$ |
| CCl$_4$ absorption | 60% w/w |
| Strength | 9 N · cm$^{-1}$ (Method BS 2576) |
| Fabric weight | 90 to 110 g · m$^{-2}$ |
| Intermediate layers 10, 12 | |
| Type | Non-woven fabric Viscose rayon 95% Polyester 5% |
| Fabric weight | 45 to 65 g · m$^{-2}$ |
| Fiber staple length | 50 mm |

| Cover layers 4, 6 OPTION 1 | |
| --- | --- |
| Type | Point sealed non-woven fabric Polypropylene core; polyethylene sheath |
| Fabric weight | 50 g · m$^{-2}$ |
| Sealed area | not more than 14% |
| OPTION 2 | |
| Type | Spun laid non-woven fabric with acrylic binder 100% polyamide |
| Fabric weight | 35 g · m$^{-2}$ |

The bicomponent mentioned above as option 1 for the cover layer is preferred where assembly is by welding and the fabric is required to maintain its integrity in the region of the welds.

The central layer 8 and the intermediate layers 10, 12 are bonded to one another by means of a net like construction of 100% thermo fusible fibres, by the application of heat and pressure.

The resistance to air flow of the filter was measured using the method described above. The temperature and humidity of air breathed through the filter installed over a tracheostoma using a meter (such as one sold under the trade mark HM34CX by Viasala), with the probes inserted and sealed through the filter device, into the tracheostoma. The results of the tests, compared with those from a patient able to breathe normally, were as follows:

| | AIR RESISTANCE (kPa · s · l$^{-1}$) | TEMPERATURE (°C.) | HUMIDITY |
| --- | --- | --- | --- |
| Breathing via nose | 0.5 | 35.8 | 85% |
| Breathing via tracheostoma | 0.7 | 34.5 | 83% |

Figure 8:
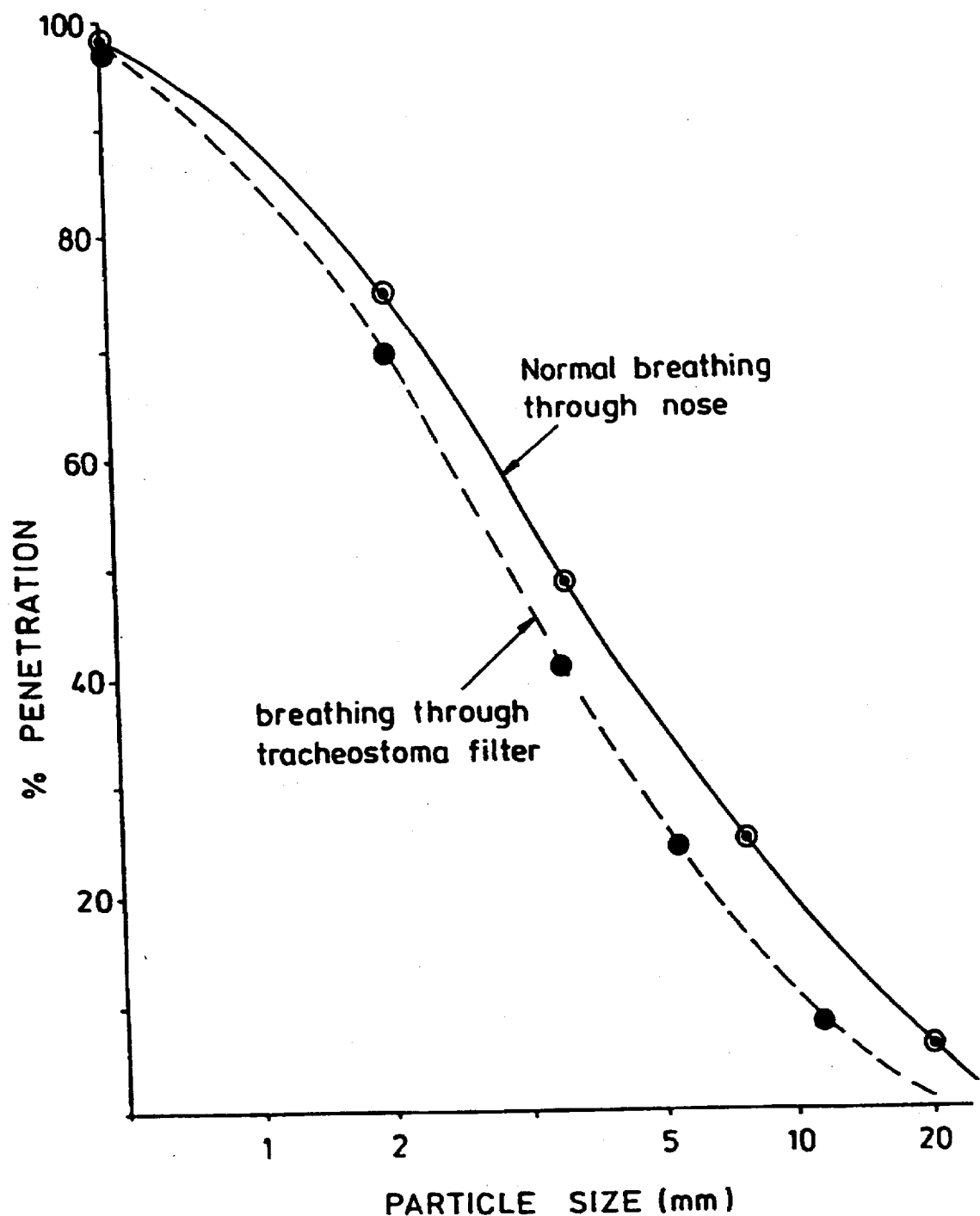
FIG. 8 is a graph showing the filtering characteristics of the filter shown in FIGS. 1 to 3.

FIG. 8 shows the characteristics of the filter shown in FIGS. 1 to 3 compared to the nasal function of a human being, plotted in terms of the percentage of particles of given size that are filtered by the filter and the nose respectively. It will be seen that the filtration characteristics of the device follow very closely those of the human nose. Furthermore, the pressure drop across the filter device is very close to that found in normal human breathing.

I claim:

1. A filter device to filter air that is to be breathed through a tracheostoma, which comprises:

(a) a first zone for filtering matter filtered in a normal nasal cavity from air passing through the filter, (b) a second zone which provides means of exchange of heat and moisture with the air, said first and second zones providing resistance to air flow through the zones of the device of at least about 0.2 kPa.s.l$^{-1}$, and (c) sealing means for forming a seal between the device and the stoma substantially continuously around the periphery of the device so as substantially to prevent leakage of air around the sides of the device between the device and the stoma, and so that the device provides the resistance to air flow in breathing when in use on both inhalation and exhalation.

2. A device as claimed in claim 1, in which the first zone of the filter comprises an activated carbon material.

3. A device as claimed in claim 2, in which the carbon material is provided as an activated carbon fabric.

4. A device as claimed in claim 1, in which the first zone of the filter comprises a fabric whose fibres are charged.

5. A device as claimed in claim 4, in which the second zone of the device comprises material.

6. A device as claimed in claim 5, in which the hydrophilic material comprises regenerated cellulose material.

7. A device as claimed in claim 6, in which the second zone of the filter comprises fibrous material.

8. A device as claimed in claim 7, in which the filter size of the first zone is greater than about $0.5 \times 10^{-6}$ m.

9. A device as claimed in claim 8, which includes a pre-filter having a filter size that is larger than that of the first zone of the filter.

10. A device as claimed in claim 9, which includes at least one cover layer.

11. A device as claimed in claim 10, which includes formations for mounting a tracheostoma valve.

12. A device as claimed in claim 11, which includes a housing in which the filter zone of the device, intended for filtering matter filtered in a normal nasal cavity from air passing through the filter, is received.

13. A device as claimed in claim 12, in which the housing includes means for receiving a valve.

14. A device as claimed in claim 13, in which the resistance to air flow through the device is less than about $1.0$ kPa.s.l$^{-1}$.

15. A device as claimed in claim 14, in which the means for forming a seal comprises a quantity of an adhesive material.

16. A device as claimed in claim 2, which includes a carrier, particulate carbon being provided on a surface of said carrier.

17. A device as claimed in claim 16, in which the carrier is porous and has interstices formed therein, the particulate carbon being provided in said interstices.

18. A filter device to filter air that is to be breathed through a tracheostoma, said filter comprising:

(a) a first zone for filtering matter filtered from air passing through said filter;

(b) a second zone to exchange heat and moisture with the air passing through said filter; and (c) a seal to support said filter in place over the tracheostoma and to form a seal between said filter and the tracheostoma, said seal being provided around a periphery of the filter so as substantially to prevent leakage of air around sides of the device between the device and the tracheostoma, and to provide resistance to air flow under both inhalation and exhalation, wherein said first and second zones provide a resistance of more than about $0.2$ kPa.s.l$^{-1}$ to air flowing through said first and second zones.

* * * * *

UNITED STATES PATENT AND TRADEMARK OFFICE
CERTIFICATE OF CORRECTION

PATENT NO. : 5,666,950

DATED : SEPTEMBER 16, 1997

INVENTOR(S) : SMITH

It is certified that error appears in the above-identified patent and that said Letters Patent is hereby corrected as shown below:

Col. 9, line 6, claim 5: insert --a hydrophilic-- after the word "comprises"

Signed and Sealed this

Twelfth Day of May, 1998

Attest:

BRUCE LEHMAN

*Attesting Officer*  *Commissioner of Patents and Trademarks*